United States Patent [19]

Chen et al.

[11] Patent Number: 5,250,563
[45] Date of Patent: Oct. 5, 1993

[54] INHIBITORS OF HIV PROTEASE

[75] Inventors: Shieh-Shung T. Chen, Morganville; George A. Doss, Westfield; Russell B. Lingham, Watchung, all of N.J.

[73] Assignee: Merck & Co., Inc., Rahway, N.J.

[21] Appl. No.: 951,927

[22] Filed: Sep. 25, 1992

Related U.S. Application Data

[63] Continuation of Ser. No. 765,627, Sep. 25, 1991, abandoned.

[51] Int. Cl.$^5$ .................. A61K 31/40; C07D 209/56
[52] U.S. Cl. .................. 514/411; 548/437; 435/119
[58] Field of Search .................. 548/437; 514/411

[56] References Cited

U.S. PATENT DOCUMENTS 3,849,437 11/1974 Ousby et al. .................. 548/437
5,183,826 2/1993 Bills et al. .................. 514/411

FOREIGN PATENT DOCUMENTS 0001924 1/1972 Japan .
90/13293 11/1090 PCT Int'l Appl. .

OTHER PUBLICATIONS

Kohl, N. E. et al., "Active HIV Protease is required for viral infectivity," Proc. Natl. Acad. Sci., 85, 4686 (1988).
Ratner, L. et al., "Complete Nucleotide Sequence of the AIDS Virus, HTLV-III, " Nature 313, 277 (1985).
Toh, H. et al., "Close Structural Resemblance . . . ," EMBO J. 4, 1267 (1985).
Power, M. D. et al., "Nucleotide Sequence of SRV-1 . . . ," Science 231, 1567 (1986)
Pearl, L. H. et al., "A structural model for the retroviral proteases," Nature 329, 351 (1987).

*Primary Examiner*—Joseph Paul Brust
*Assistant Examiner*—MarySusan H. Gabilan
*Attorney, Agent, or Firm*—Roy D. Meredith; Charles M. Caruso

[57] ABSTRACT

Novel cytochalasins are the biotransformed products after incubation with a substrate in a culture of the microorganism Kibdelosporangium sp. (Merck Culture Collection MA 6559), ATCC No. 53771. The compounds of the present invention inhibit HIV protease and are useful in the prevention or treatment of infection by HIV and the treatment of AIDS, either as a compound, pharmaceutically acceptable salt, pharmaceutical composition ingredient, whether or not as a prodrug or as a combination with other antivirals, anti-infectives, immunomodulators, antibiotics or vaccines.

9 Claims, No Drawings

INHIBITORS OF HIV PROTEASE

This is a continuation of application Ser. No. 07/765,627 filed Sep. 25, 1991, now abandoned.

This case is related to Merck case application Ser. No. 07/587,812.

The present invention is concerned with compounds of Formula A which inhibit the protease encoded by human immunodeficiency virus (HIV). The compounds, or pharmaceutically acceptable salt thereof, are of value in the prevention of infection by HIV, the treatment of infection by HIV and the treatment of the resulting acquired immune deficiency syndrome (AIDS). The present invention also relates to pharmaceutical compositions containing the compounds, and to a method of use of the present compounds with or without other agents for the treatment of AIDS & viral infection by HIV.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Interruption of this processing prevents the production of normally infectious virus. For example, Kohl, N. E., et al., Proc. Natl. Acad. Sci. USA 85, 4686 (1988) demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

Nucleotide sequencing of HIV shows the presence of a pol gene in one open reading frame [Ratner, L. et al., Nature, 313, 277(1985)]. Amino acid sequence homology provides evidence that the pol sequence encodes reverse transcriptase, an endonuclease and an HIV protease [Toh, H. et al., EMBO J. 4, 1267 (1985); Power, M. D. et al., Science, 231, 1567 (1986); Pearl, L. H. et al., Nature 329, 351 (1987)].

Applicants demonstrate that the compounds of this invention are inhibitors of HIV protease.

BRIEF DESCRIPTION OF THE INVENTION

Biotransformed compounds of Formula A are disclosed. The compounds are useful in the inhibition of HIV protease, the prevention of infection by HIV, the treatment of infection by HIV and in the treatment of AIDS and/or ARC, either as compounds, pharmaceutically acceptable ester or salt thereof (when appropriate), pharmaceutical composition ingredients, whether or not as prodrugs or as a combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION

This invention is concerned with the compounds of Formula A, or pharmaceutically acceptable salts or esters thereof, in the inhibition of HIV protease, the prevention or treatment of infection by HIV and in the treatment of the resulting acquired immune deficiency syndrome (AIDS). The biotransformed compounds are the products of the incubation of substrate compound 1 with the microorganism Kibdelosporangium sp. (Merck Culture Collection MA 6559) ATCC No. 53,771. Thus, substrate compound I, of the structure

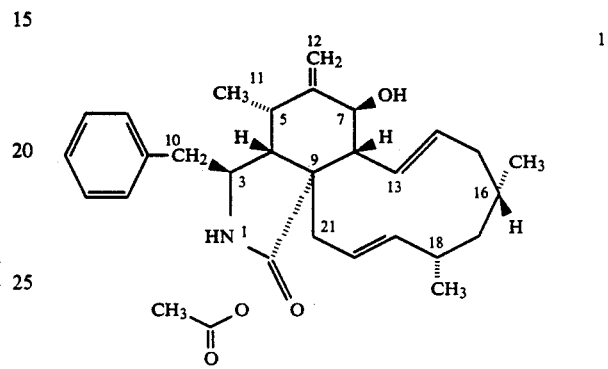

is biotransformed to compounds of Formula A, as follows:

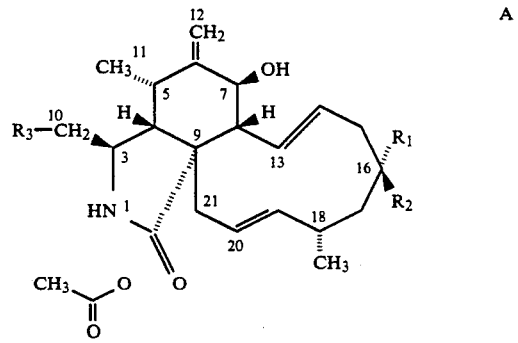

wherein:
R$_1$ is CH$_2$OH;
R$_2$ is H or OH; and
R$_3$ is phenyl, 4-hydroxyphenyl, 3-hydroxyphenyl or 3,4-dihydroxyphenyl;
or pharmaceutically acceptable salt or ester thereof.

One embodiment of this invention is the compound of formula A wherein R$_1$ is CH$_2$OH, R$_2$ is H, and R$_3$ is phenyl.

Another embodiment of this invention is the compound of formula A wherein R$_1$ is CH$_2$OH, R$_2$ is H, and R$_3$ is 4-hydroxyphenyl.

Another embodiment of this invention is the compound of formula A wherein R$_1$ is CH$_2$OH, R$_2$ is H, and R$_3$ is 3-hydroxyphenyl.

Another embodiment of this invention is the compound of formula A wherein R$_1$ is CH$_2$OH, R$_2$ is H, and R$_3$ is 3,4-dihydroxyphenyl.

Another embodiment of this invention is the compound of formula A wherein R$_1$ is CH$_2$OH, R$_2$ is OH, and R$_3$ is phenyl.

Another embodiment of this invention is the compound of formula A wherein $R_1$ is $CH_2OH$, $R_2$ is OH, and $R_3$ is 3-hydroxyphenyl.

In the structures of 1 and formula A, it is noted parenthetically that the keto group attached to C-1 is 'behind' and not directly bound to the carbon-oxygen bond of C-21.

The pharmaceutically-acceptable salts of the compounds of the present invention (in the form of water- or oil-soluble or dispersible products) include the conventional non-toxic salts or the quaternary ammonium salts of these compounds, which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Hydrates or esters are also encompassed by the present invention. Such hydrates or esters are those which would readily occur to the skilled artisan, and include, for example, $C_{1-4}$alkyl esters.

It is to be noted that in the fermentation reactions disclosed herein and the post-treatment of the fermentation mixture the conformational and/or stereo isomer(s) of Compound 1 due to asymmetric carbon atom(s) or double bond(s) of Compound 1 may occasionally be transformed into the other conformational and/or stereoisomer(s), and such cases are also included within the scope of the present invention.

The compounds of the present inventions are useful in the inhibition of HIV protease, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids, bites, accidental needle stick, or exposure to patient blood during surgery.

For these purposes, the compounds of the present invention may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Dosage levels of the order of 0.1 to 5.0 or 10.0 grams-per-day are useful in the treatment or prevention of the above-indicated conditions, with oral doses two times higher. For example, infection by HIV is effectively treated by the administration of from 50 to 250 milligrams of the compound per kilogram of body weight from one to three times per day. It will be understood, however, that the specific dose level and frequency of dosage for any particular patient may be varied and will depend upon a variety of factors including the activity of the specific compound employed, the metabolic stability and length of action of that compound, the age of the patient, body weight, general health, sex, diet, mode and time of administration, rate of excretion, drug combination, the severity of the particular condition, and the host undergoing therapy.

The present invention is also directed to combinations of the HIV protease inhibitor compounds with one or more agents useful in the treatment of AIDS. For example, the compounds of this invention may be effectively administered, whether at periods of pre-exposure and/or post-exposure, in combination with effective amounts of other AIDS antivirals, immunomodulators, anti-infectives, or vaccines.

FERMENTATION OF COMPOUND 1 WITH MA 6559

The present invention involves the fermentation of Kibdelosporangium sp., MA 6559 together with compound 1 to produce Compounds of Formula A. The microorganism is currently on deposit with the American Type Culture Collection, 12301 Parklawn Drive in Rockville, Md. as ATCC No. 53771, and in the Merck Culture Collection in Rahway, N.J. as MA 6559. The physical characteristics and taxonomy, including morphological, cultural, biological and physiological characteristics are briefly described hereinbelow.

On the basis of the taxonomic analysis performed thus far, the culture has been tentatively assigned in the order Actinomycetales and in the family Actinoplanacea. Further taxonomic characteristics are being examined to place this organism conclusively within a genus and species.

This culture grows well on routine media including trypticase soy agar (28° and 37° C.), yeast malt extract agar, glycerol asparagine agar, inorganic salt starch agar, oatmeal agar, Czapek Dox, solution and peptone agars and Bennett's agar, all at 28° C., but poorly on tap-water agar.

Morphology

This Gram stain positive culture grows as a branched filamentous mycelium with a diameter of 0.57–0.76 microns. Colonies are opaque, raised, and erose. Colony texture is rubbery on yeast malt extract agar but tends to be butyrous on other media where significant fragmentation of the mycelium is observed. The colony surface tends to be powdery in appearance. No diffusable pigments were observed.

Sporangia are produced on all but tap-water agar, are predominantly spherical and range in size from 9–12 microns in diameter. They tend to rupture easily. Sporangia are generally visible by 21 days and tend to coalesce on glycerol asparagine agar. Spores are rod-shaped with blunt ends (0.76×1.98 microns), non-motile and occur in long, unbranched chains of up to 150 microns in length.

Chemotaxonomic Studies

Peptidoglycan was found to contain meso-diaminopimelic acid. Whole cell hydrolysates contain arabinose, galactose, mannose and traces of rhamnose (Type IV cell wall).

Miscellaneous Physiological Reactions

The culture does not produce melanoid pigments. A soluble, non-pH dependent red pigment is produced on glycerol asparagine agar and on carbon source utilization media where growth is observed (see below). Starch is hydrolyzed. Carbon source utilization pattern is as follows: good growth on D-arabinose, L-arabinose, cellobiose, D-fructose, i-inositol, $\alpha$-D-lactose, $\beta$-D-lactose, D-maltose, D-mannitol, D-mannose, D-raffinose, sucrose, and D-xylose; no growth on L-rhamnose or L-xylose.

Diagnosis

Key characteristics that differentiate MA6559 from Streptomyces species are cell wall composition (meso-diaminopimelic acid vs. LL-diaminopimelic acid) and mode of sporulation (production of sporangia vs. chains of arthrospores). Although pseudosporangia have been reported to occur in some Streptomyces species, all Streptomyces have LL-diaminopimelic acid in the peptidolycan. Only one genus has been previously described that has cell wall type IV and produce sporangia: Kibdelosporangium (Shearer, Colman, Ferrin, Nesbit and Nash, International J. Syst. Back. 36, 47–54 (1986). On the basis of the above-described chemotaxonomic and morphological data, MA6559 is a novel strain of this monospecific genus that differs from the type species (*Kibdelosporangium aridum*) on a number of characteristics including: production of melanoid, soluble and mycelial bound pigments, hydrolysis of starch and utilization of rhamnose.

Cultural characteristics of MA 6559 Yeast Extract-Malt Extract Agar (ISP Medium 2)

Vegetative mycelium is hyaline to yellow, aerial mycelium develops by 14d and is buff to rose-pink and powdery in appearance. The reverse side is tan to reddish brown.

Oatmeal Agar (ISP Medium 3)

Vegetative mycelium is hyaline to yellow, the reverse side is hyaline to tan. Aerial growth is white to light rose-beige and powdery in appearance.

Inorganic Salts-Starch Agar (ISP Medium 4)

Light growth, scant aerial mycelium. Vegetative growth is hyaline and highly fragmented. Clearing of starch occurs at periphery of colonies noted by 7 d.

Glycerol Asparagine Agar (ISP Medium 5)

Vegetative growth is hyaline to yellow, the reverse side is hyaline to cinnamon brown. Aerial mycelium is powdery and white to rose-pink.

Peptide-Iron-Yeast Extract Agar (ISP Medium 6)

Vegetative growth is tan. No aerial growth observed, no melanoid pigments produced.

Tyrosine Agar (ISP Medium 7)

Vegetative growth is tan becoming deep purple as culture ages. Aerial mycelium is velvety to grayed rose-beige.

Czapek-Dox Agar

Vegetative growth is tan with a pink tone as the culture ages. Aerial mycelia are short and matted with a moist appearance.

The present invention process can be practiced with any Formula A compound-producing strain of Kibdelosporangium sp. and particularly preferred is the ATCC No. 53771 strain.

In general, Formula A compounds can be produced by culturing incubating or fermenting the Formula A compound-producing strain with substrate compound 1 in an aqueous nutrient medium containing sources of assimilable carbon and nitrogen, preferably under submerged aerobic conditions (e.g. shaking culture, submerged culture, etc.). The aqueous medium is preferably maintained at a pH of about 7 at the initiation and termination (harvest) of the fermentation process. A higher pH leads to substantial and/or total loss of product. The desired pH may be maintained by the use of a buffer such as morpholinoethanesulfonic acid (MES), morpholinopropanesulfonic acid (MOPS), and the like, or by choice of nutrient materials which inherently possess buffering properties, such as production media described hereinbelow.

The preferred sources of carbon in the nutrient medium are carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form, because less pure materials which contain traces of growth factors and considerable quantities of mineral nutrients, are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

As to the conditions for the production of Formula A compounds in massive amounts, submerged aerobic cultural conditions are preferred therefor. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of Formula A compounds. Accordingly, it is desirable first to produce a vegetative inoculum of the organism by inoculating a relatively small quantity of culture medium with spores or mycelia of the organism produced in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of Formula A compounds and is generally autoclaved to sterilize the medium prior to inoculation. The pH of the medium is generally adjusted to about 7.0 prior to the autoclaving step by suitable addition of an acid or base, preferably in the form of a buffering solution.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 20° C. and 40° C., preferably 25°–35° C., for a period of about 20 hours to 24 hours, which may be varied according to fermentation conditions and scales. These longer fermentation times are employed to insure substantial. biotransformation of Compound 1. Preferably, the production cultures are incubated for about 24 hours at 27° C. on a rotary shaker operating at 220 rpm, wherein the pH of the fermentation medium is maintained at 7.0 to harvest.

Preferred culturing/production media for carrying out the fermentation include the following media:

|  | g/l |
|---|---|
| Seed Medium A | |
| Dextrose | 1.0 |
| Dextrin | 10.0 |
| Beef Extract | 3.0 |
| Ardamine pH | 5.0 |
| NZ Amine Type E | 5.0 |
| $MgSO_4.7H_2O$ | 0.05 |
| $K_2HPO_4$ | 0.37 |
| Adjust pH to 7.1 | |
| Add $CaCO_3$ 0.5 g/l | |
| Transformation Medium B | |
| Glucose | 10 |
| Hycase SF | 2 |
| Beef Extract | 1 |
| Corn Steep Liquor | 3 |
| Adjust pH to 7.0 | |

The produced Formula A compounds can be recovered from the culture medium by conventional means which are commonly used for the recovery of other known biologically active substances. The produced Formula A compounds are found in the cultured mycelium and filtrate, and accordingly can be isolated and purified from the mycelium and the filtrate, which are obtained by filtering or centrifuging the cultured broth, by a conventional method such as concentration under reduced pressure, lyophilization, extraction with a conventional solvent, such as methanol and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred method is solvent extraction, particularly using methanol.

PRODUCTION OF SUBSTRATE COMPOUND 1

Compound 1, which is the substrate, is conveniently produced by cultivating Hypoxylon fragiforme MF 5510 or MF 5511 in the culture collection of Merck & Co., Rahway, N.J. which have been deposited under the Budapest Treaty in the Culture Collection of the American Type Culture Collection at 12301 Parklawn Drive, Rockville, Md. 20852, and assigned accession numbers ATCC 20994 and ATCC 20995. Compound 1 and its production is the subject of related application Merck Case, U.S. Ser. No. 07/587,812, filed Sep. 25, 1990.

The fungus which may be obtained by collection of its stromata from the bark of recently dead American beech (*Fagus grandifolia*) as hereinafter described may be described as follows:

Stromata erumpent through the bark, gregarious to confluent, often converging over extensive areas of the bark surface, hemispherical to pulvinate, with papillate ostioles, dry, dull, pinkish cinnamon to brick-red when young, Fawn Color (capitalized color names from Ridgway, R. Color Standards and Nomenclature, Washington, D.C. 1912). Avellaneous, Vinaceous-Russet, becoming dull reddish brown or grayish brown in age Wood Brown, Army Brown, Sorghum Brown, Pecan Brown, finally developing some blackish colors from deposit of discharged ascospores and decomposition of outer surface, occasionally with minute tufts of Nodulosporium condiophores. Stromatal tissue extremely brittle, carbonaceous, purplish black to black. Perithecia 0.1–0.3 mm in diameter, pyriform to subglobose, with papillate ostioles. Asci 8-spored, uniseriate, narrowly cylindrical, stipitate, 110–175×6–9 µm, with an amyloid apical ring. Ascospores purplish black in mass, olive-brown to olive gray in 3% KOH, ellipsoid-inequilateral with narrowly rounded ends, 10–14.5×5.5–7.5 µm, with 1–5 guttulae.

In culture, colonies attain 55–60 mm on potato-dextrose agar (Difco) in one week at 20° C. Colonies with relatively sparse aerial hyphae and abundant submerged hyphae, somewhat transparent, downy to thinly tomentose, with surface developing a mealy, granulose, or pustulate texture in age, hyaline at first but soon becoming pale grayish cream, grayish buff, developing patches of buff or cinnamon, Pale Ochraceous Buff, Light Ochraceous Buff, Light Pinkish Cinnamon, Pinkish Cinnamon, Cinnamon where conidial development occurs. Reverse becoming deeply pigmented due to exudate in the medium, ranging from pale yellow, yellowish green, Barium Yellow, Napthalene Yellow, Citron Yellow, Yellowish Citron, to dark green, blackish green, or black, Serpentine Green, Dull Blackish Green.

A conspicuous Nodulosporium conidial stage is formed in culture, as well as on the stromata in nature. Conidiophores (on corn-meal agar, Difco) are macronematous, or occasionally micronematous, more or less erect, rigid, 240–500 µm tall, 3.5–6 µm in diameter, generally without a well-defined axis, branching 1–8 times in a sympodial pattern, occasionally verticillately branched in the terminal branches, with walls smooth to minutely verruculose, hyaline to pale olive-brown in 3% KOH. Conidogenous cells are borne as terminal branches singly or in groups of 2–3, or as lateral branches originating from subtending septa, cylindrical or slightly clavate, polyblastic, with faint, minute denticles remaining after conidial dehiscence. Conidia are 5–6×3–4.5 µm, subpyriform, obovate, or ellipsoid-inequilateral, dry, hyaline, smooth, slightly truncate because of the basal scar, in groups of 4–10 at the terminus of the conidiogenous cell.

The habitat, stromata, conidial stage, and culture morphology were identical in two separate isolates and agree well with published descriptions (S. C. Jong, 1972, Washington Agriculture Experiment Station Technical Bulletin 17; R. W. G. Dennis, 1981, British Ascomycetes).

The fungus H. fragiforme having the foregoing properties may be found on the bark of various hardwood trees, and is especially common on recently dead beech. Usually extensive areas of the bark will be covered with fruiting bodies called stromata. Within the stromata, perithecia develop which, when mature, produce forcibly-discharged ascospores. The ascospores may be applied to standard agar media, allowed to germinate and then cultivated to obtain the compound of the present invention.

The ascospores may be obtained from the stromata which are actively discharging spores by fixing the stromata to tops of petri dishes containing yeast-malt extract agar supplemented with streptomycin sulfate and tetracycline and permitting the ascospores to discharge directly onto the agar surface from the stromata for a few hours and then allowing the ascospores to germinate.

When the perithecia are not actively discharging ascospores, the stromata containing the perithecia may be dissected and the ascospores carefully lifted and transferred to an isolation medium. The isolated culture then may be employed to inoculate a cultivation medium for the production of the desired product.

In culture, the fungus is white to pale gray with appressed mycelium which rapidly (about a week) covers the surface of the culture medium and which subsequently exudes a dark green to black pigment. After about two weeks it develops pale cinnamon colors in the lower portions of the aerial mycelium which corresponds to the onset of the development of the Nodulosporium conidial stage. At this point, the mycelial fragments or conidia may be transferred to malt-yeast extract slants and frozen for storage or employed for cultivation by inoculating a culture medium.

Compound 1 may be obtained by cultivating H. fragiforme ATCC 20994 or 20995 in a suitable nutrient medium under conditions hereinafter described until a substantial amount of the product is formed in the culture medium, harvesting by extracting the active component from the fermentation medium with a suitable solvent, concentrating the solution containing the desired component, then subjecting the concentrated material to chromatographic separation to isolate Compound 1 from other metabolites and impurities.

The cultivation of H. fragiforme ATCC 20994 or 20995 to produce Compound 1 may be carried out in a nutrient medium containing sources of carbon and nitrogen assimilable by the microorganism and also containing low levels of inorganic salts. The medium may be supplemented with trace metals, although if complex sources of carbon and nitrogen are employed, the trace metals are usually present in the complex sources.

Suitable sources of carbon include glycerol, sugars, sugar alcohols, starches and other carbohydrates, or carbohydrate derivatives such as dextran, cerelose, as well as complex nutrients such as oat flour, corn meal, millet, corn and the like. The exact quantity of the carbon source which is utilized in the medium will depend, in part, upon the other ingredients in the medium, but it is usually found that an amount of carbohydrate between 0.5 and 40 percent by weight of the medium is satisfactory. These carbon sources can be used individually or several such carbon sources may be combined in the same medium.

The sources of nitrogen include amino acids such as glycine, arginine, threonine, methionine and the like, ammonium salt, as well as complex sources such as yeast hydrolysates, yeast autolysates, yeast cells, tomato paste, soybean meal, casein hydrolysates, yeast extracts, corn steep liquors, distillers solubles, cottonseed meal, meat extract, and the like. The various sources of nitrogen can be used alone or in combination in amounts ranging from 0.2 to 10 percent by weight of the medium.

Among the nutrient inorganic salts, which can be incorporated in the culture media are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

Typical useful media are given below. In the preparation of liquid media, distilled water is used. The pH is adjusted prior to sterilization at 121° C. for 20 minutes. Where calcium carbonate is a component, the pH is adjusted prior to the addition of calcium carbonate unless otherwise indicated.

Liquid Media

| Component | (g/l) | Component | (g/l) |
|---|---|---|---|
| Medium C | | Medium D (PBGG1) | |
| Glucose | 10.0 | Glycerol | 75.0 |
| Fructose | 15.0 | Glucose | 10.0 |
| Sucrose | 40.0 | "Ardamine"* PH | 5.0 |
| "NZ amine"* Type E | 4.0 | $(NH_4)_2SO_4$ | 2.0 |
| Urea | 4.0 | Soybean meal | 2.0 |
| $K_2HPO_4$ | 0.5 | Tomato paste | 5.0 |
| KCl | 0.25 | Sodium citrate | 2.0 |
| $MgSO_4.7H_2O$ | 0.25 | Polyglycol P2000** | 2.0 ml/l |
| $ZnSO_4.7H_2O$ | 0.9 | | |
| $CaCO_3$ | 8.0 | | |
| pH 7.0 | | pH 7.0 | |
| *Casein hydrolysate | | *Yeast autolysate | |
| Sheffield Products | | Yeast Products Inc. | |
| Kraft, Inc. | | Clifton, NJ: "Ardamine" | |
| | | trademark assigned to | |
| | | Champlain Industries, Inc. | |
| | | **Dow Chemical Co. | |
| Medium E (NPA-4) | | Medium F (NPA-8) | |
| Asparagine | 1.0 | Asparagine | 1.0 |
| "Edamin"* | 2.5 | Yeast extract | 1.0 |
| "Primatone" HS** | 2.5 | Glucose | 10.0 |
| Yeast extract | 5.0 | $CaCO_3$ | 5.0 |
| Malt extract | 10.0 | | |
| Sucrose | 5.0 | | |
| $CaCO_3$ | 5.0 | | |
| pH 7.2–7.4 | | pH 7.2–7.4 | |
| *Lactalbumin hydrolysate | | | |
| Sheffield Products, | | | |
| Kraft, Inc. | | | |
| **Meat hydrolysate | | | |
| Sheffield Products | | | |
| Medium G (KF) | | | |
| | | Trace Elements | |
| Corn steep liquor | 5.0 | $FeSO_4.7H_2O$ | 1.0 |
| Tomato paste | 40.0 | $MnSO_4.4H_2O$ | 1.0 |
| Oat flour | 10.0 | $CuCl_2.2H_2O$ | 0.025 |
| Glucose | 10.0 | $CaCl_2.H_2O$ | 0.1 |
| Trace elements | 10.0 ml | $H_3BO_3$ | 0.056 |
| | | $(NH_4)_6MoO_{24}.4H_2O$ | 0.019 |
| pH 6.8 | | $ZnSO_4.7H_2O$ | 0.2 |
| | | Prepare in 0.6N HCl | |
| Medium H (3) | | | |
| | | Trace Elements | |
| Glucose | 10.0 | $FeCl_3.6H_2O$ | 5.8 |
| Glycerol | 20.0 | $MnSO_4.H_2O$ | 0.1 |
| Dextrin | 5.0 | $CoCl_2.6H_2O$ | 0.02 |
| Urea | 2.0 | $CuSO_4.5H_2O$ | 0.015 |
| $NaNO_3$ | 2.0 | $NaMoO_4.2H_2O$ | 0.012 |
| Yeast extract | 1.0 | $ZnCl_2$ | 0.02 |
| $Na_2HPO_4$ | 0.5 | $SnCl_2.2H_2O$ | 0.005 |
| $MgSO_4.7H_2O$ | 1.0 | $H_3BO_3$ | 0.01 |
| $CaCl_2.2H_2O$ | 0.5 | KCl | 0.02 |
| Trace elements | 1.0 ml/l | HCl (concentrated) | 2.0 ml/l |
| Medium I (NPA-1) | | | |
| | | Mineral Salts | |
| Corn gluten | 5.0 | KCl | 0.74 |
| "Edamin" | 2.5 | $CaCl_2.2H_2O$ | 0.02 |
| "Primatone" HS | 2.5 | $NaH_2PO_4$ | 1.4 |
| Yeast extract | 1.0 | Citric acid | 0.38 |
| Glucose | 10.0 | $MgCl_2.6H_2O$ | 0.25 |
| Mineral salts | 250 ml/l | $Na_2SO_4$ | 0.36 |
| $CaCO_3$ | 5.0 | Trace elements solution | 50 ml/l |
| $CaCO_3$ added after pH to 7.2 to 7.4 | | pH to 7.2 to 7.4 | |
| Trace Elements | | | |
| $FeCl_3.6H_2O$ | 5.4 | | |
| $MnCl_2.2H_2O$ | 2.0 | | |
| $CuCl_2.2H_2O$ | 0.17 | | |
| $CoCl_2.6H_2O$ | 0.48 | | |
| $H_3BO_3$ | 0.06 | | |

-continued

| Component | Liquid Media (g/l) | Component | (g/l) |
|---|---|---|---|
| $Na_2MoO_4.2H_2O$ | 0.2 | | |
| Prepared in 0.6 N HCl | | | |
| Medium J (NPA-3) | | | |
| Corn gluten | 5.0 | | |
| Yeast extract | 5.0 | | |
| Malt extract | 10.0 | | |
| Sucrose | 5.0 | | |
| Mineral salts | 250 ml/l Same as above for Medium G | | |
| $CaCO_3$ | 5.0 | | |
| | | Medium K | |
| | | | K Elements |
| Glucose | 10.0 | $FeCl_3.6H_2O$ | 5.8 |
| Glycerol | 20.0 | $MnSO_4.H_2O$ | 0.1 |
| Dextrin | 5.0 | $CoCl_2$ | 0.2 |
| Urea | 2.0 | $CuSO_4.5H_2O$ | 0.015 |
| $NaNO_3$ | 2.0 | $Na_2MoO_4.2H_2O$ | 0.012 |
| Yeast Extract | 1.0 | $ZnCl_2$ | 0.02 |
| $Na_2HPO_4$ | 0.5 | $SnCl_2.2H_2O$ | 0.005 |
| $MgSO_4.7H_2O$ | 1.0 | $H_3BO_3$ | 0.01 |
| $CaCl_2$ | 0.5 | KCl | 0.02 |
| K Elements | 1.0 ml/l | HCl (Conc) | 2.0 ml/l |
| Adjust pH = 7.0 | | | |

Solid Media

Suitable solid media may be prepared by coating vermiculite with a liquid phase medium such as Medium C. In using solid phase for growth, the liquid medium is inoculated and the inoculated medium intimately contacted with sterilized vermiculite to coat the vermiculite. Generally from about 400 to 450 milliliters of liquid medium is employed for about 1200 cubic centimeters of vermiculite.

Alternatively, solid media may be based on complex solid nutrients. Typical such media are given below. In the preparation of solid media, distilled water is used in the preparation of the base liquid. No pH adjustment is necessary. The medium is sterilized at 121° C. for 15 minutes. When cool, 15.0 ml of distilled water is added to each flask and autoclaved an additional 20 minutes to provide solid media ready for use in production.

| Medium L (F-1) | |
|---|---|
| Component | |
| Cracked corn | 10.0 g/flask |
| Base liquid* | 10.0 ml/flask |
| *Base liquid | (g/l) |
| "Ardamine" PH | 0.2 |
| $KH_2PO_4$ | 0.1 |
| $MgSO_4.7H_2O$ | 0.1 |
| $FeSO_4.7H_2O$ | 0.01 |
| $ZnSO_4.7H_2O$ | 0.01 |
| Medium M (F204) | |
| Component | |
| Millet | 15.0 g/flask |
| Base liquid* | 10.0 ml/flask |
| *Base liquid | (g/l) |
| Yeast extract | 50.0 |
| Monosodium glutamate | 10.0 |
| Corn oil | 10.0 ml |
| Sodium tartrate | 10.0 |
| $FeSO_4.7H_2O$ | 1.0 |
| Medium N (BRF) | |
| Component | |
| Brown rice | 10.0 g/flask |
| Base liquid* | 20.0 g/flask |
| *Base liquid | (g/l) |
| Yeast extract | 1.0 |
| Sodium tartrate | 0.5 |

-continued

| | |
|---|---|
| $KH_2PO_4$ | 0.5 |

The foregoing media may be employed in fermentations carried out by inoculating the selected medium with a culture growth of H. fragiforme ATCC 20994 or 20995 and cultivating as hereinafter described to produce Compound 1.

Generally, the culture growth or mycelial mass is a previously prepared and preserved frozen vegetative mycelia which is thawed and used to inoculate a seed medium and cultivated to produce the organisms as a mycelial mass which serve as seeds when inoculated in the production medium.

The seed medium may be of the following composition:

| YME SEED MEDIUM | |
|---|---|
| Component | |
| Yeast extract | 4.0 g |
| Malt extract | 10.0 g |
| Glucose | 4.0 g |
| Distilled water | 1000 ml |
| pH 7.0 | |
| (sterilized 121° C., 20 min.) | |

A medium previously listed as production Medium G and also referred to as KF medium also may be employed as seed medium.

The frozen vegetative mycelia used to inoculate seed medium may be that previously obtained by placing a slant culture of H. fragiforme in 50 milliliters of YME seed medium and incubated for 4 days at 22° C., 75 percent relative humidity and 220 rpm to obtain a biomass, portions of which are placed in sterile vials containing glycerol (to a final glycerol concentration of 10%) and frozen and maintained at −80° C.

It has been found that Compound 1 may be produced on direct incubation of the initial multi-ascospore isolate of H. fragiforme on YME agar slant for three weeks at 25° C. under fluorescent light. The biomass so produced may be inoculated in a production medium and employed in the production of Compound 1. It also may be employed to inoculate seed medium to produce greater biomass for inoculating in production media.

In the production of Compound 1, first a slant section of a culture of *H. fragiforme* ATCC 20994 or 20995 is inoculated into a nutrient seed medium of pH in the range of 5 to 8, preferably YME seed medium of pH 7.0 and the flasks incubated with agitation at temperatures in the range of from about 15° C. to about 30° C., preferably about 22° to 28° C. Agitation may be up to 400 rpm but is preferably from about 200 to 220 rpm. The incubation may be carried out over a period of from 2 to 15 days, preferably 3 to 10 days. When growth is abundant, usually between 2 and 5 days, the growth may be used to inoculate the production medium for the production of Compound 1.

If appropriate, a second stage fermentation may be carried out in the seed medium for greater production of mycelia mass by inoculating fresh seed medium with a portion of the culture growth and then incubating under similar conditions but for a shortened period. The resulting growth then may be employed to inoculate the production medium.

The fermentation production medium inoculated with the culture growth is incubated for 3 to 30 days, usually 7 to 21 days, generally with agitation. The fermentation may be conducted aerobically at temperatures ranging from about 20° C. to about 30° C. Temperatures of about 24°-28° C. are most preferred. The pH of the nutrient medium suitable for producing the instant compounds can vary from about 5.0 to 8.5 with a preferred range of from about 6.0 to 7.5.

Although a liquid medium is generally preferred for production, especially on a large scale, a solid medium provides a more natural environment for the *H. fragiforme* and may be employed in production of the compound. One of the solid media previously named may be employed, or a liquid medium may be inoculated and the inoculated medium coated onto vermiculite and treated as a natural solid medium.

When the production is carried out on vermiculite pooled with the nutrient medium, a portion of the seed is used to inoculate an appropriate liquid medium and the inoculated medium coated on the vermiculite. Conveniently, the liquid medium and vermiculite may be intimately contacted in a roller jar on a roller machine for time sufficient to effect a substantially uniform coating then incubated for time sufficient to effect the desired production. Generally, this is carried out by incubating on a roller assembly for about 4 to 24 days at 22°-25° C. at 75% relative humidity. Sometimes, the incubation may be carried out initially at the higher temperature, e.g. at 25° C. for 4 to 6 days and thereafter at the lower temperature.

When the solid medium is based on complex solid nutrients, the seed medium is used to inoculate the solid medium in a conventional manner and the resulting medium incubated for 3 to 30 days, preferably 7 to 21 days, with agitation, generally about 200 to 400 rpm, preferably about 220 rpm, at 22° to 25° C.

After completion of the cultivation period, as can be determined by HPLC of the cultivation medium, generally 12 to 18 days, the product is recovered from the production medium and thereafter isolated. The exact steps may vary somewhat depending on whether the fermentation is carried out in liquid or solid medium, what solvent is employed and what adsorbent or combination of adsorbents is employed.

When the fermentation has been carried out on a solid medium, the first step generally is adding a solvent to the medium and thoroughly mixing to extract the cultivation products from the solid. Suitable solvents for the extraction are polar solvents such as acetone, methyl ethyl ketone, methanol, isopropanol and the like. The mixture is then filtered to remove the solid and to obtain the product in the filtrate. The filtrate is concentrated under reduced pressure to obtain crude product as residue.

The residue is dissolved in an oxygenated solvent and placed on a chromatographic column for the separation steps. Suitable columns are silica gel, silica based reverse phase and dextran gel.

When the fermentation has been carried out in a liquid medium, the fermentation medium is filtered to recover mycelial cells. The cells are extracted several times and the combined extracts are subjected to reduced pressure to obtain the product as residue. Suitable solvents for extraction include ethyl acetate, methyl ethyl ketone, acetone and methanol.

The product residue is purified by chromatography, preferably on silica gel, but also on silica based reverse phase and dextran gel and the like. It may be carried out by dissolving the residue in methylene chloride and acetone, charging to a silica gel column, washing with hexane and eluting with hexane/acetone with increasing concentrations of acetone. The cuts may be monitored by HPLC and the cuts containing most of the product, combined and then taken to dryness. The residue is dissolved in methylene chloride and the chromatographic purification process repeated. This may be repeated further, if necessary. Compound 1 may be obtained in crystalline form when the product rich cuts are combined, concentrated, and the product allowed to crystallize from the solution.

Other solvent systems which may be employed in chromatographic purification and crystallization are methylene chloride/ethyl acetate, methylene chloride/methanol and the like.

EXAMPLE 1

A. Fermentation

A frozen vial (2.0 ml) of culture MA6559 was used to inoculate a 250 ml baffled shake flask containing 50 ml of medium A. The seed flask was incubated on a rotary shaker (220 rpm) at 27° C. for 24 hours. A 2.5 ml aliquot of the developed seed was used to inoculate a 250 ml non-baffled flask containing 50 ml of transformation medium B; compound 1 in DMSO/MeOH was added to the fermentation at 0 hour to achieve a final concentration of 0.05 mg/ml. The shake flasks were subsequently incubated at 27° C. on a rotary shaker for 30 hours.

The resultant whole broth was extracted as described in Section B.

| Media | g/l |
|---|---|
| Seed Medium A | |
| Dextrose | 1.0 |
| Dextrin | 10.0 |
| Beef Extract | 3.0 |
| Ardamine pH | 5.0 |
| NZ Amine Type E | 5.0 |
| MgSO$_4$.7h$_2$O | 0.05 |
| K$_2$HPO$_4$ | 0.3 |
| Adjust pH to 7.1 | |
| Add CaCO$_3$.5 g/l | |

-continued

| Media | g/l |
| --- | --- |
| Transformation Medium B | |
| Glucose | 10 |
| Hycase SF | 2 |
| Beef Extract | 1 |
| Corn Steep Liquor | 3 |
| Adjust pH to 7.0 | |

B. Isolation and Purification

The whole broth (200 ml) was extracted with methylene chloride (3×200 ml). Methylene chloride extracts were combined and concentrated under vacuum to an oily residue. The residue was dissolved in methanol and subjected to high performance liquid chromatography (HPLC). HPLC was carried out on Whatman Partisil 10 ODS-3,9.4 mm×25 cm column at 45° C. and monitored at 215 nm. The column was developed at 3 ml/min with a linear gradient from $H_2O$—$CH_3CN$, 80:20 to $H_2O$—$CH_3CN$, 20:80 in 40 minutes. The compounds were collected during repeated injections of the above described extract. The fractions at retention time, 26.1,29.2 30.0, 31.2 and 35.4 minutes, were pooled, respectively, and evaporated to yield 1.0 mg of compound 5, 0.9 mg of 3 1.3 mg of 4, 0.8 mg of 6 and 1.0 mg of compound 2, respectively.

EXAMPLE 2

Characterization

The Structure Of Six Novel Cytochalasins Produces By Microbial Transformation Of Compound 1

The structures of six microbial transformation products of the cytochalasin 1 have been determined by NMR spectroscopy. All six metabolites were found to have undergone hydroxylation at the C-16 methyl group of 1($R_1$=$CH_2OH$). Three of the compounds, 3,4 and 5, have been further hydroxylated at the para, the meta, and both the para and the meta, positions of the phenyl ring, respectively. Metabolites 6 and 7 were shown to result from vicinal dihydroxylation on both C-16 and its attached $CH_3$. The latter metabolite 7 was also hydroxylated on the meta position of the phenyl ring. See Table I.

The stereochemistry of hydroxylation at C-16 in 6 and 7 was shown to have led to retention rather than inversion of the configuration C-16.

The structure were established by $^1H$, $^{13}C$ and various 2D NMR techniques; particularly the distinction between the three methyls at C-5, C-16, and C-18, as possible sites for hydroxylation. Unambiguous assignments of $^1H$ and $^{13}C$ chemical shifts of the metabolites as well as the parent compound itself have been established. The key NMR features that lead to the structure determination of these compounds include the following:

A. Hydroxylation at C-16 methyl.

The $^1H$ NMR spectrum 2 revealed the low absence of one methyl signal and the appearance of two novel protons at ~3.44 ppm consistent with a $CH_2OH$, indicating that hydroxylation at one of the three methyl groups at C-5, C-16 or C-18 in 1 had occurred. To determine which methyl group had been hydroxylated, a complete analysis of the $^1H$ NMR spectrum had to be carried out. All proton signals of 2 as well as the parent compound 1 were unambiguously assigned by means of COSY and TOCSY experiments. Analysis of the $^1H$—$^1H$ coupling network in 2 unequivocally indicated that the affected methyl was attached to C-16 rather than C-5 or C-18. For example, the two remaining methyl doublets in 2 were correlated in the COSY spectrum with two protons at 2.2 and 2.8 ppm,

TABLE I

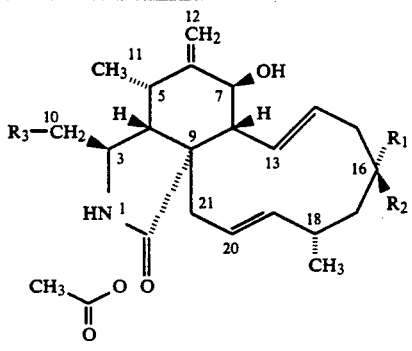

| Compd | $R_1$ | $R_2$ | $R_3$ |
| --- | --- | --- | --- |
| 1 | $CH_3$ | H | phenyl |
| 2 | $CH_2OH$ | H | phenyl |
| 3 | $CH_2OH$ | H | 4-hydroxyphenyl |
| 4 | $CH_2OH$ | H | 3-hydroxyphenyl |
| 5 | $CH_2OH$ | H | 3,4-dihydroxyphenyl |
| 6 | $CH_2OH$ | OH | phenyl |
| 7 | $CH_2OH$ | OH | 3-hydroxyphenyl | each of which was further correlated to an olefinic signal, thus indicating that these methyls must be at C-18 and C-5 and not C-16. All other COSY correlations supported the proposed structure.

The structure of 2 was confirmed by the $^{13}C$ NMR spectrum which, compared with that of the parent 1, indicated the loss of one of the methyl signals at 25.1 ppm and the appearance of a new methylene signal at 68.2 ppm consistent with a $CH_2OH$ group. The $^{13}C$ signals of C-15 and C-17 were both shifted upfield (by ~3 ppm) due to the γ-effect of the new hydroxy group. In contrast, C-16 signal was shifted downfield (by ~8 ppm) as expected for the β-effect of the OH group. All other signals were virtually unaffected.

B. Hydroxylation at the phenyl ring:

In addition to hydroxylation at C-16 methyl group described above, hydroxylation of the phenyl ring in 3, 4, and 5 was also discovered. The aromatic region of these compounds showed splitting patterns characteristic of 1,4-, 1,3- and 1,3,4-substituted benzenes, indicating hydroxylation at the para, the meta, and both the para and the meta carbons of the phenyl ring, respectively. The upfield shift of the protons ortho and/or para to the hydroxy groups confirm these assignments. An alternative structure for 5 wherein $R_3$=2,5-dihydroxyphenyl, is unlikely.

C. Hydroxylation at C-16;

Compounds 6 and 7 have been shown to result from a vicinal dihydroxylation at C-16-$CH_3$. Compound 1 was also hydroxylated at the meta position of the phenyl ring. Compared with 2, the $^1H$ NMR spectra of 6 and 7 showed a simpler splitting pattern for the $CH_2OH$ protons (a broad AB system at 3.39 ppm) suggesting the absence of H-16. The COSY spectra supported the proposed structure as the $CH_2OH$ methylene protons showed no coupling to any other signal except to an exchangeable OH proton at 1.9 ppm; the cross peaks to H-16 at 1.21 (cf. 2) were absent. Except for the aromatic region, the $^1$H NMR spectra of 6 and 7 were virtually identical.

The structure of 6 was confirmed by $^{13}$C NMR. The C-16 (methine) signal was conspicuously absent at ~40 ppm and a new quaternary signal at 75.0 ppm has appeared instead, strongly indicating hydroxylation at this carbon. Compared with 2, the signals of C-15, C-17, and the CH$_2$OH were shifted downfield, whereas C-18 was shifted upfield, in agreement with the $\beta$ and $\gamma$ effects of the new OH group at C-16.

The stereochemistry of C-16 in 6 and 7 was retained during hydroxylation. Irradiation of the CH$_2$OH methylene protons in 7, resulted in NOE enhancement of only C-15 and C-17 protons. Examining a molecular model of 7 (based on the x-ray crystal structure of 1), it was clear that such NOE results are consistent with the 16S (retention) and not the 16R (inversion) configuration. The latter would have exhibited strong NOE enhancements of H-14, H-18, and, to a lesser extent, H-19 which showed close proximity to the irradiated protons in the 16R model. Furthermore, these very same protons were shifted downfield in 6 and 7 compared with 2, a result explained by the deshielding effect of the nearby (axial) C-16—OH in the 16S configuration.

D. Conclusion:

The above structure determinations in Table I relied on unambiguous $^1$H and $^{13}$C signal assignment of the metabolites as well as the parent compound 1 itself. Such assignments were achieved by $^1$H—$^1$H COSY, TOCSY, $^1$H-$^{13}$C correlation via one-bond and long range couplings.

EXAMPLE 3

Preparation of Substrate, Compound 1

A. Mycelium from the initial multi-ascospore isolate of *H. fragiforme* was inoculated onto 15 milliters of Difco yeast-malt extract agar (containing 41 grams of extract per liter) slanted in a 50 milliliter polypropylene tube sealed with a cotton plug. The culture was grown at 25° C. in continuous fluorescent light for 3 weeks to obtain secondary metabolites in the culture medium.

The contents of the tube were then extracted with 8 milliliters of methyl ethyl ketone. The solvent was then removed from the extract and the residue containing metabolite was dissolved in 0.1 milliliter of a mixture of 99 percent DMSO and 1 percent tris(hydroxymethyl)aminomethane (TRIS) buffer.

The sample showed detectable inhibition of HIV protease.

B. A slant culture of *H. fragiforme* was placed in 50 milliliters of YME seed medium contained in a 250 milliliter Erlenmeyer flask. The resulting medium was incubated for 4 days at 22° C., 75 percent relative humidity and 220 rpm on a 2 inch throw gyratory shaker to obtain a biomass. Portions of the biomass were placed into sterile vials containing glycerol (final glycerol concentration of 10%) and were frozen and maintained at −80° C.

One frozen vial was thawed to room temperature and used to inoculate 50 milliliters of YME seed medium; the resulting inoculated medium was incubated at 22° C. at 220 rpm for 4 days. The resulting biomass was asceptically macerated with 12 millimeter porcelain balls, and 24 milliliters of the slurry was placed into 425 milliliters of production Medium C and production Medium K. Each production medium was shaken to disperse the biomass and was added to a 110×535 millimeter roller culture vessel which contained 1250 cubic centimeters of large-particle vermiculite. The roller culture vessel was shaken to distribute the contents and was incubated on a roller assembly at 22° C., 75 percent relative humidity for 19 days to obtain a secondary metabolite in the fermentation medium.

After the incubation period, the solid fermentation material was mechanically removed from the walls of the roller jar, 700 milliliters of methyl ethyl ketone added and the roller jar capped. The fermentation mixture was extracted by placing the jar horizontally on the roller jar apparatus for about one-half hour. The methyl ethyl ketone extract containing the secondary metabolite was filtered and the filtrate subjected to reduced pressure to remove the solvent and to recover as residue, the secondary metabolite.

The residue was dissolved in 50 percent methyl ethyl ketone and methanol. A portion of the solution on being tested in an HIV protease inhibitor assay showed inhibitory activity.

C. A frozen vegetative mycelia (FVM) of *H. fragiforme* prepared as described in part B of this Example (see above) was employed in the following cultivation.

YME seed medium (50 ml) was inoculated with 1.0 milliliter of the FVM of *H. fragiforme* and grown on a gyratory shaker (220 rpm; 5.1 cm throw) for four days at 25° C. The culture grew as a mycelial mass which was broken prior to cultivation by adding 10 small sterile ceramic balls and 5 small sterile, ceramic cylinders and incubating on a gyratory shaker for 30 minutes.

Aliquots of 24 milliliters of the seed were used to inoculate each 4-liter roller jar production vessels containing Medium C and the inoculated vessels incubated on a roller machine at 25° C. for 4 days, and thereafter at 22° C. for 15 days.

The contents of each of the four 4-liter roller jars containing the solid substrate fermentation were extracted with 500 milliliters of methyl ethyl ketone for two hours at 100 rpm, then filtered to obtain the methyl ethyl ketone extract. The extract was concentrated to dryness under reduced pressure and the residue dissolved in 20 milliliters of 1:1 acetone:methylene chloride. Sixteen milliliters of the solution was chromatographed on a 500 milliliter silica gel (E. Merck) column in 4:1 hexane:acetone and eluted successively with 2 column volumes (CV) of hexane:acetone 4:1; followed by 1 CV of each of 3:1 and 1:1 hexane:acetone. About 40 cuts were taken and bioassayed in the HIV protease-inhibitor assay. Activity was found in cuts 18-21, amounting to about 350 milliliters and corresponding to 2.2 to 2.8 CV. The foregoing fractions were taken to dryness under reduced pressure to obtain 600 milligrams of white powder.

The powder was dissolved in methanol and allowed to crystallize. About 300 milligrams of crystals were recovered and the purity determined by HPLC (Spectra Physics 8700) on a one milligram sample using a 60:40 acetonitrile:water solvent system at 40° C. on a Whatman-ODS-3 (4.6 mm×25 cm, 5 μm) colum at a flow rate of 1 ml/minute monitored by UV at 213 and 243 nm to obtain the purified Compound 1 with a retention time of 12.1 minutes. A portion of the crystals was subjected to thin-layer chromatography using 3:1 hexane:acetone eluting solvent for a 5×20 cm silica-gel (E. Merck) plate. The compound had a $R_f$ of 0.25 (strained orange when sprayed with 50 percent sulfuric acid and heated).

A sample was submitted for bioassay in a peptide cleavage assay and was found to have an IC$_{50}$ of about 3 μg/ml in an HIV protease assay.

One milliliter of a frozen culture of *H. fragiforme* ATCC 20994 was transferred into a 250 milliliter Erlenmeyer flask containing 50 milliliters of YME seed medium and the inoculated medium cultivated at 25° C. and 220 rpm for 96 hours. At the end of this time, 10 milliliters of the culture was transferred to a 2-liter plain flask containing 500 milliliters of YME medium and the resulting medium cultivated at 25° C. and 180 rpm. Then, 150 milliliters of the culture were transferred to a 23 liter fermenter vessel containing 15 liters of YME medium. The fermenter was operated at 25° C., 300 rpm, air flow of 4.5 liters/minute and a back pressure of 0.35 bar for approximately 48 hours. At the end of this period, 2.5 liters of broth were aseptically transferred to a 70-liter vessel containing 50 liters of PBGG-1 (modified) medium of the following composition:

| Component | Concentration (g/l) |
| --- | --- |
| Glycerol | 75.0 |
| Cerelose | 30.0 |
| "Ardamine" PH | 5.0 |
| Ammonium Sulfate | 2.0 |
| Soybean Meal | 5.0 |
| Tomato Paste | 5.0 |
| Sodium Citrate | 2.0 |
| Polyglycol 2000 | 2.0 ml/l |
| pH = 7.0 | |

The inoculated medium was cultivated for 72 hours at which time the pH adjusted from 4.4 to 6.0 with dilute NaOH. Cultivation was continued; after 100 hours, the pH of the broth had risen to 7.5. During the remaining cultivation period (to 220 hours), the pH of the culture was manually adjusted with dilute H$_2$SO$_4$ to maintain the level below 7.5. The rpm was adjusted as needed from an initial value of 300 to maintain a dissolved oxygen level of 30 percent and to provide better mixing.

The broth obtained from the foregoing fermentation was filtered through Dicaitite (diatomite, product of Grefco Minerals) and the cells extracted twice with ethyl acetate. The ethyl acetate solution was concentrated under reduced pressure at 40° C. to obtain an oil which then was dissolved in 800 milliliters of methylene chloride and acetone and charged to a funnel containing 1.5 kg of silica gel (Davidson). The funnel was washed with 1 liter of hexane and then eluted successively with 4 liters of 4:1 hexane/acetone, 4 liters of 3:1 hexane/acetone, and 4 liters of acetone, and the eluates subjected to HPLC analysis using the same column and solvent system used in Example 3. Most of the compound was found in Cut 1 (1 liter) and the remainder was found in Cuts 6 to 9.

Cut 1 was taken to dryness under reduced pressure at 40° C. and the residue dissolved in 200 milliliters of methylene chloride and charged to a silica gel funnel containing 1.2 kg of silica gel and eluted with the same solvent system. The desired compound was found in Cuts 4 to 7 of this elution. About 3.6 grams of Compound 1 crystallized from Cut 4. The remaining cuts were combined and reduced to a small volume and filtered. From the filtrate 32 grams of white solid was obtained which contained over 12 grams of Compound 1. This was dissolved in 150 milliliters of methylene chloride and charged to a 2.5 liter silica gel (Davidson) column containing 2.5 liters of silica gel in 4:1 hexane/acetone. The product was eluted from the column using successively 3 liters of 4:1, 6 liters of 6:1 and 3 liters of 1:1 hexane/acetone. Cuts 6–22 amounting to 5.25 liters contained Compound 1. The cuts were pooled, concentrated to a small volume and filtered to obtain 12.75 grams of white crystalline product. The identity of the product was confirmed by TLC on a 5×20 cm silica gel (E. Merck) plate using 3:1 hexane/acetone as eluting solvent and obtaining an R$_f$ 0.25 (orange with sulfuric acid) and by HPLC, again on a Whatman-ODS-3 (4.6 mm×25 cm, 5 μm) column at a flow rate of 1 milliliter per minute and monitored by UV at 213 and 243 nm and obtaining a retention time of 12.1 min.

EXAMPLE 4

Assay for Inhibition of Recombinant HIV Protease

Inhibition studies were performed on the reaction of the HIV protease expressed in Escherichia coli with a tritiated peptide substrate, [$^3$H]-acetyl-Val-Ser-Gln-Asn-(beta-napthyl-Ala)-Pro-Ile-Val-Gin-Gly-Arg-Arg-NH$_2$(MW 1800). The two arginine residues at the carboxyl terminus give this peptide an overall positive charge at acidic pH and enable it to bind to the H+ form of DOWEX AG-50W-X8 resin and similar resins. The HIV protease cleaves between the β-napthyl-Ala and proline residues to yield a product ($^3$H-acetyl-val-ser-asn-(β-napthyl-ala) that is either neutral or slightly negatively charged and does not bind to the cation exchange resin. It is therefore possible to conveniently separate the labelled product from the substrate.

Aliquots of 25 μl containing 6.0–8.0 nM HIV protease in assay buffer (100 mM sodium acetate, pH 5.5 and 0.1% BSA) are placed in assay tubes. The reaction is initiated by addition of 25 μl aliquots of 4.2 μM tritiated peptide substrate in 100 mM sodium acetate, pH 5.5. After incubation for 60 minutes at 37° C., the reaction is stopped with 100 μl of 5% H$_3$PO$_4$, then analysed by application of column chromatography.

| Compound | IC$_{50}$(μM) |
| --- | --- |
| 1 | 10 |
| 2 | 43 |
| 3 | 40 |
| 4 | 25 |
| 5 | >50 |
| 6 | >50 |
| 7 | >50. |

EXAMPLE 5

1000 compressed tablets each containing 500 mg of any of Compounds 2–7 are prepared from the following formulation:

| Compound | Grams |
| --- | --- |
| Compound 2–7 | 500 |
| Starch | 750 |
| Dibasic calcium phosphate hydrous | 5000 |
| Calcium stearate | 2.5 |

The finely powdered ingredients are mixed well and granulated with 10% starch paste. The granulation is dried and compressed into tablets.

EXAMPLE 6

1000 hard gelatin capsules, each containing 500 mg of any of Compounds 2-7 are prepared from the following formulation:

| Compound | Grams |
|---|---|
| Compound 2-7 | 500 |
| Starch | 750 |
| Dibasic calcium phosphate hydrous | 5000 |
| Calcium stearate | 2.5 |

A uniform mixture of the ingredients is prepared by blending and used to fill two-piece hard gelatin capsules.

EXAMPLE 7

250 ml of an injectable solution are prepared by conventional procedures having the following formulation:

| | |
|---|---|
| Dextrose | 12.5 g |
| Water | 250 mL |
| Compound 2-7 | 400 mg |

The ingredients are blended and thereafter sterilized for use.

EXAMPLE 8

An aerosol composition may be prepared having the following formulation:

| | Per Canister |
|---|---|
| Compound 2-7 | 24 mg |
| Lecithin NF Liquid Concentrated | 1.2 mg |
| Trichlorofluoromethane, NF | 4.026 g |
| Dichlorodifluoromethane, NF | 12.15 g |

While the foregoing specification teaches the principles of the present invention, with examples provided for the purposes of illustration, it will be understood that the practice of the invention encompasses all of the usual variations, adaptations, or modifications, as come within the scope of the following claims and its equivalents.

We claim:

1. A compound of the formula

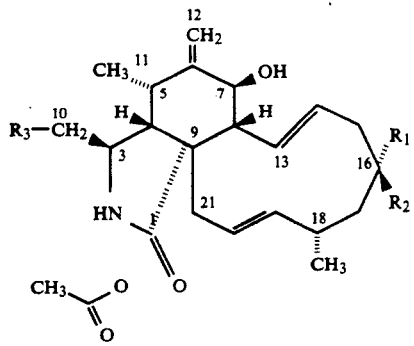

wherein:
$R_1$ is $CH_2OH$;
$R_2$ is H or OH; and
$R_3$ is phenyl, 4-hydroxyphenyl, 3-hydroxyphenyl or 3,4-dihydroxyphenyl;
or pharmaceutically acceptable salt or ester thereof.

2. A compound of claim 1, wherein $R_1$ is $CH_2OH$, $R_2$ is H, and $R_3$ is phenyl.

3. A compound of claim 1, wherein $R_1$ is $CH_2OH$, $R_2$ is H, and $R_3$ is 4-hydroxyphenyl.

4. A compound of claim 1, wherein $R_1$ is $CH_2OH$, $R_2$ is H, and $R_3$ is 3-hydroxyphenyl.

5. A compound of claim 1, wherein $R_1$ is $CH_2OH$, $R_2$ is H, and $R_3$ is 3,4-dihydroxyphenyl.

6. A compound of claim 1, wherein $R_1$ is $CH_2OH$, $R_2$ is OH, and $R_3$ is phenyl.

7. A compound of claim 1, wherein $R_1$ is $CH_2OH$, $R_2$ is OH, and $R_3$ is 3-hydroxyphenyl.

8. A pharmaceutical composition comprising a therapeutically effective amount of a compound as in any of claims 1-7 and a pharmaceutically acceptable carrier.

9. A method of inhibiting HIV protease, comprising administering to a mammal an effective amount of a compound of as in any of claims 1-7.

* * * * *